(12) United States Patent
Sausen et al.

(10) Patent No.: US 10,016,205 B2
(45) Date of Patent: Jul. 10, 2018

(54) BI-DIRECTIONAL REAMER ASSEMBLY (71) Applicant: Greatbatch Ltd., Clarence, NY (US)

(72) Inventors: Kari Ann Sausen, Clarence, NY (US);
Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 198 days.

(21) Appl. No.: 15/231,338

(22) Filed: Aug. 8, 2016

(65) Prior Publication Data

US 2017/0035443 A1 Feb. 9, 2017

Related U.S. Application Data (60) Provisional application No. 62/202,506, filed on Aug. 7, 2015.

(51) Int. Cl.
*A61B 17/16* (2006.01)

(52) U.S. Cl.
CPC ...... *A61B 17/1666* (2013.01); *A61B 17/1617* (2013.01); *A61B 17/1642* (2013.01); *A61B 17/1659* (2013.01); *A61B 17/162* (2013.01)

(58) Field of Classification Search
CPC . A61B 17/16; A61B 17/1666; A61B 17/1642; A61B 17/1617
See application file for complete search history.

(56) References Cited

U.S. PATENT DOCUMENTS

| 3,630,204 A | 12/1971 | Fishbein |
| 3,633,583 A | 1/1972 | Fishbein |
| 3,702,611 A | 11/1972 | Fishbein |
| 4,023,572 A | 5/1977 | Weigand et al. |
| 4,116,200 A | 9/1978 | Braun et al. |
| 4,131,116 A | 12/1978 | Hedrick |
| 4,621,637 A | 11/1986 | Fishbein |
| 4,802,468 A | 2/1989 | Powlan |
| 4,811,632 A | 3/1989 | Salyer |
| 5,100,267 A | 3/1992 | Salyer |
| 5,116,165 A | 5/1992 | Salyer |
| 5,203,653 A | 4/1993 | Kudla |

(Continued)

FOREIGN PATENT DOCUMENTS

| EP | 1933725 | 6/1988 |
| EP | 0574701 | 5/1993 |

(Continued)

OTHER PUBLICATIONS

Extended European Search, Application 16183201.9, dated Nov. 24, 2016.

*Primary Examiner* — Christopher Beccia
(74) *Attorney, Agent, or Firm* — Steven W. Winn (57) ABSTRACT An orthopedic reamer cutting tool is disclosed. The reamer is constructed having a hemispherical cutting shell that extends from an equatorial base to an apex. A plurality of cutting teeth, each having a primary tissue cutting surface, extend from the exterior surface of the cutting shell. A plurality of retractable blades, each having a secondary tissue cutting surface, are supported on a rotatable cam positioned at the base of the shell. Rotation of the cam in one of a clockwise or counterclockwise direction causes the retractable blades to extend through respective slits that extend through the thickness of the reamer shell. Rotation of the cam in the opposite direction causes the retractable blades to retract through the slits, back into the interior of the shell.

22 Claims, 10 Drawing Sheets

(56) References Cited

U.S. PATENT DOCUMENTS

| | | |
|---|---|---|
| 5,376,092 A | 12/1994 | Hein et al. |
| 5,658,290 A | 8/1997 | Lechot |
| 5,755,719 A | 5/1998 | Frieze et al. |
| 5,897,558 A | 4/1999 | Frieze et al. |
| 5,976,144 A | 11/1999 | Fishbein et al. |
| 6,027,503 A | 2/2000 | Khalili et al. |
| 6,106,536 A | 8/2000 | Lechot |
| 6,221,076 B1 | 4/2001 | Albrektsson et al. |
| 6,283,971 B1 | 9/2001 | Temeles et al. |
| 6,409,732 B1 | 6/2002 | Salyer |
| 6,428,543 B1 | 8/2002 | Salyer |
| 6,475,221 B1 | 11/2002 | White et al. |
| 6,764,490 B1 | 7/2004 | Szabo |
| 7,011,662 B2 | 3/2006 | Lechot et al. |
| 7,220,264 B1 | 5/2007 | Hershberger |
| 7,621,915 B2 | 11/2009 | Frederick et al. |
| 7,850,691 B2 | 12/2010 | Lechot |
| 8,407,880 B2 | 4/2013 | Stamp |
| 8,435,243 B2 | 5/2013 | White et al. |
| 2005/0085821 A1 | 4/2005 | Wolford |
| 2009/0163921 A1 | 6/2009 | Lechot et al. |
| 2010/0145342 A1 | 6/2010 | Grace et al. |
| 2013/0267957 A1 | 10/2013 | Stamp |

FOREIGN PATENT DOCUMENTS

| | | |
|---|---|---|
| EP | 1066796 | 1/2001 |
| EP | 2359755 | 8/2011 |
| EP | 2478852 | 7/2012 |

BI-DIRECTIONAL REAMER ASSEMBLY

CROSS REFERENCE TO RELATED APPLICATION

This application claims priority from U.S. Provisional Application Ser. No. 62/202,506, filed Aug. 7, 2015.

TECHNICAL FIELD

The present invention relates to the art of orthopedic cutting devices, more particularly, to a reamer device designed to remove tissue from the acetabulum.

BACKGROUND OF THE INVENTION

Reamers are devices intended to remove tissue and bone from the human body. Specifically, the reamer of the present invention is designed to remove tissue from the cotyloid cavity of the acetabulum in preparation for the insertion of a hip joint supported by a prosthetic cup seated in the cavity.

In general, acetabular reamers are constructed with a continuous partially hemispherical surface. This partial hemispherical structure is ideally suited to create a cavity in which to fit a prosthetic cup. Prosthetic cups generally have a curved exterior surface that is inserted into the cotyloid cavity.

Prior art reamers are typically composed of a shell having a plurality of spaced apart teeth, each tooth having a cutting surface that outwardly extends from the shell exterior surface. The teeth of prior art reamers are designed to cut and bite into tissue and bone. However, the teeth of prior art reamers may create a reamed surface having a roughened surface. Such a roughened bone surface is generally not desirable because the roughened surface can cause an implant (not shown) to not be properly seated within the cavity. In addition, a roughened reamed surface may increase physical wear of an implant which decreases the implant's service life and increases the need for additional implant replacement surgeries. The present invention, therefore, provides a reamer cutting device having multiple tissue cutting surfaces arranged in various orientations that help ensure a smooth reamed surface.

SUMMARY OF THE INVENTION

The present invention is an orthopedic reamer designed to cut and remove tissue and bone material. The device is designed to efficiently remove tissue and bone to thereby create a cavity for the insertion of an orthopedic implant. Specifically, the present invention is directed to a reamer that is preferably designed to remove tissue and bone from the acetabulum.

The reamer of the present invention comprises a reamer assembly that connects to a reamer shaft. The reamer assembly further comprises a partially hemispherical shell having a rotational axis that extends through a hemispherical sidewall of the shell. The rotational axis extends from an apex of the shell to an equatorial rim that circumferentially extends about the axis. The hemispherical sidewall is constructed with a plurality of openings that extend through a shell thickness. Each of the openings has a raised portion that forms a primary tissue cutting surface. In addition, a plurality of spaced apart slit openings extends through the shell thickness.

A plurality of spaced apart blades, each having a secondary tissue cutting surface reside within the shell interior. The blades are configured to extend or retract through a respective one of the slit openings of the shell. A cam and ring subassembly positioned at the base of the reamer shell enables the plurality of blades to extend or retract through the slit openings. In an embodiment, the ring positioned at the base of the reamer shell holds the plurality of blades in an upright position within the shell interior. The cam comprising a plurality of spaced apart ridges with ramped surfaces is positioned at the base of the reamer in contact with the blades. As the cam is rotated in either a clockwise or counter clockwise direction, the ramped surfaces of the plurality of cam ridges come into contact with a respective one of the blades, which causes the secondary tissue cutting surfaces of the blades to be raised so that they extend through the shell slit and above the shell exterior surface. Rotation of the cam in an opposite direction causes the blades and their respective secondary tissue cutting surfaces to retract within the shell interior.

The secondary tissue cutting surface may be constructed of a multitude of different cutting surfaces, such as a serrated or smooth edge surface which increases the reamer's versatility in reaming tissue and bone. In addition, the secondary tissue cutting surfaces of the retractable blades are oriented at an angle with respect to an imaginary plane intersecting the rotational axis and are preferably positioned in an opposite direction as the primary tissue cutting surfaces of the teeth. Thus, when the blades are in an extended position, tissue or bone can be cut by rotating the reamer in either a clockwise or counterclockwise direction. Thus, the reamer of the present invention enables the use of multiple cutting surfaces without the need to remove the reamer during a surgical procedure.

DETAILED DESCRIPTION OF THE PREFERRED EMBODIMENT

Figure 1:
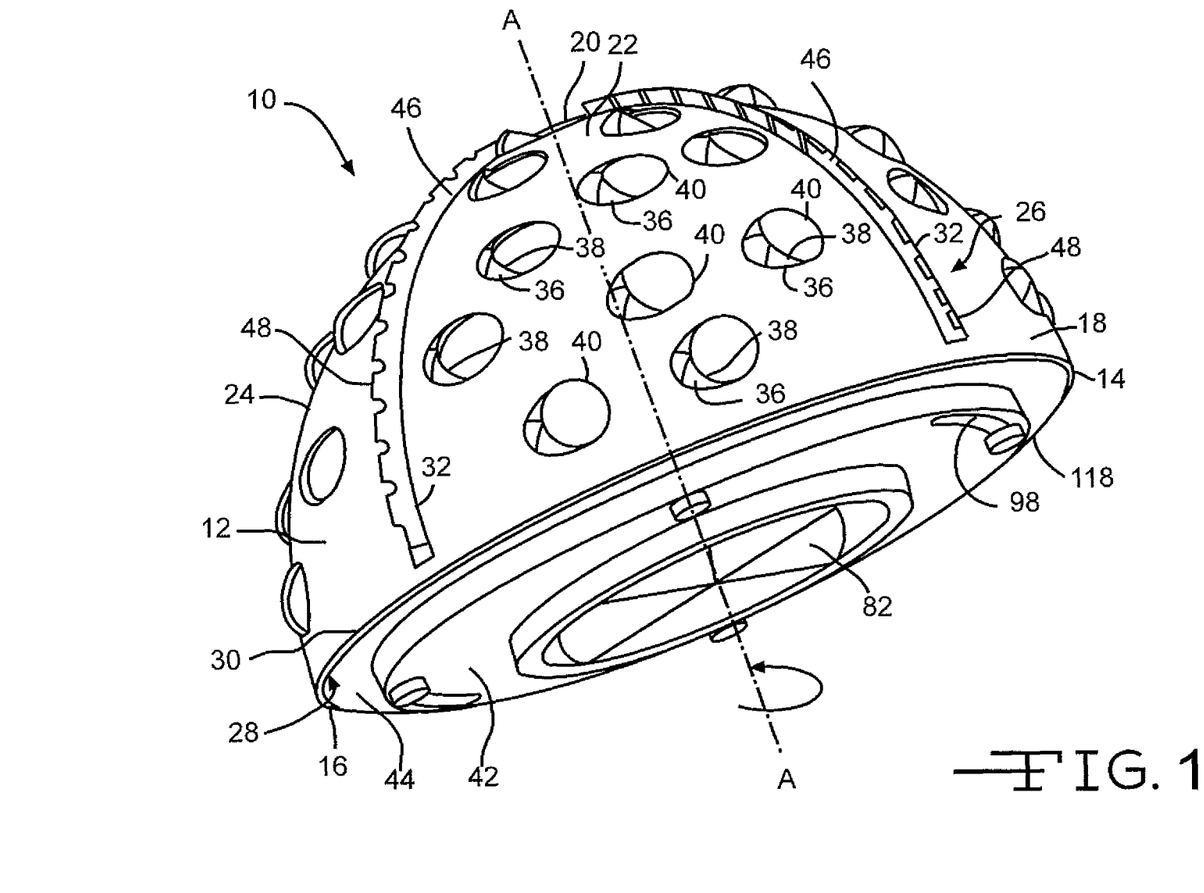
FIG. 1 illustrates a perspective view of an embodiment of a reamer of the present invention.
Figure 3A:
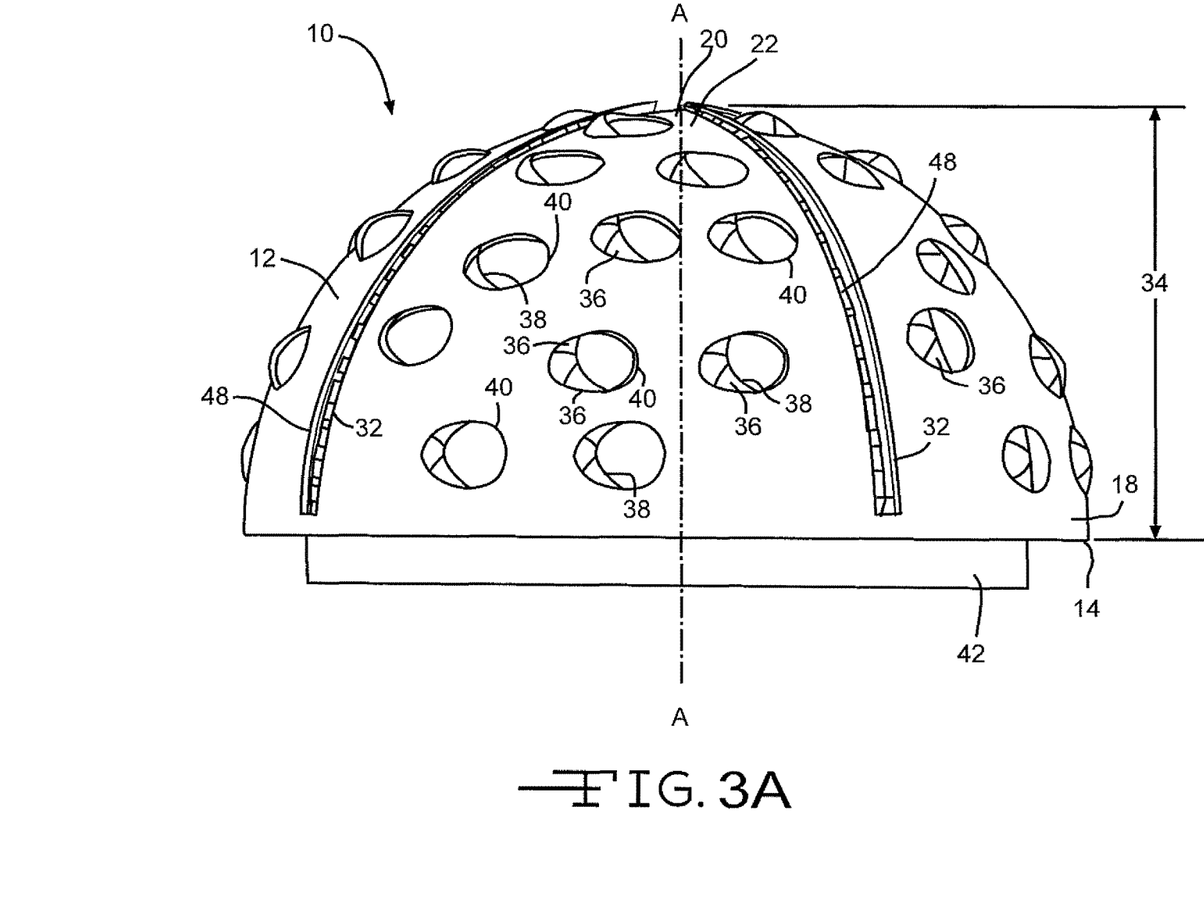
FIG. 3A illustrates a perspective view of the reamer shown in FIG. 1 with the second blades in a retracted position.
Figure 3B:
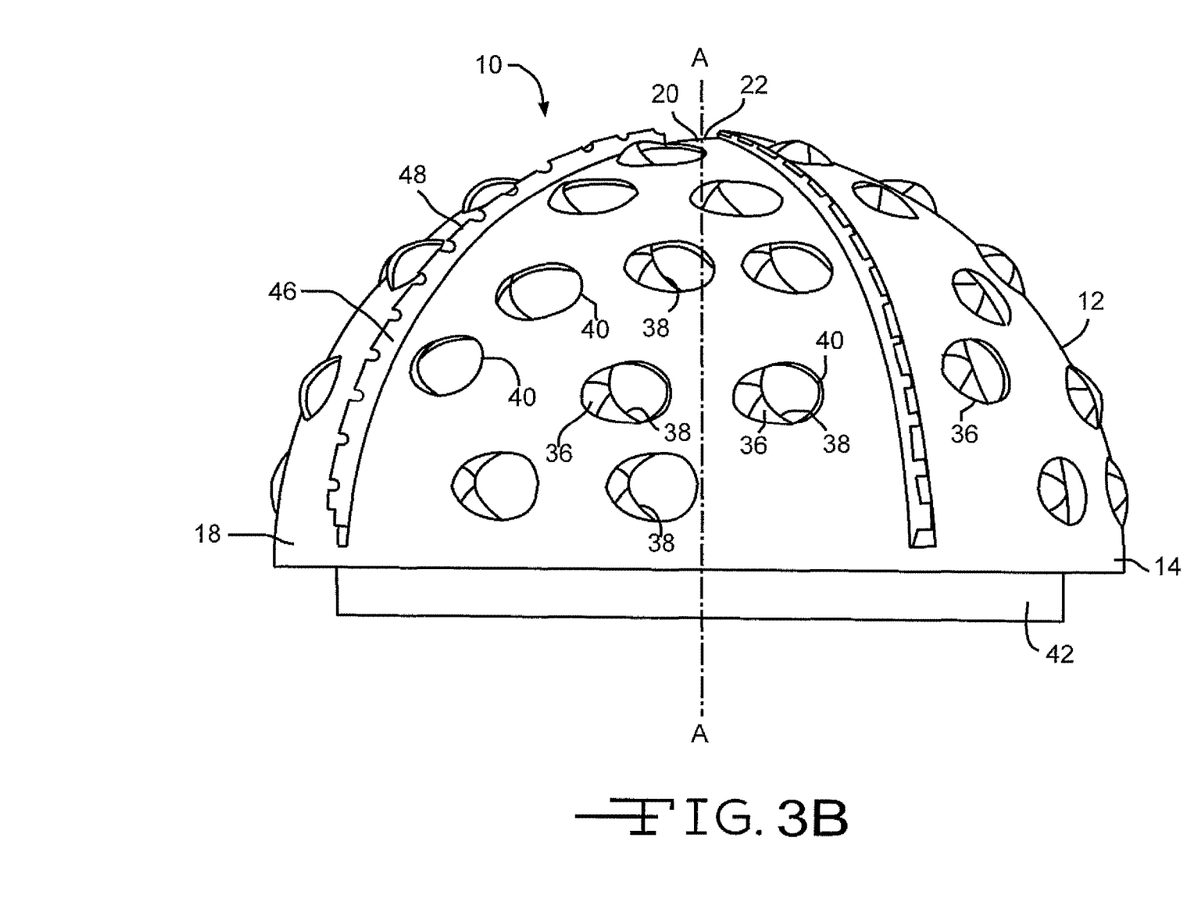
FIG. 3B illustrates a perspective view of the reamer shown in FIG. 1 with the second blades in an extended position.

Now turning to the figures, FIGS. 1, 3A and 3B illustrate a preferred embodiment of a reamer 10 of the present invention. As illustrated, the reamer 10 preferably comprises a hemispherical cutting shell 12 that extends from an equatorial base 14 at a lower edge 16 of a proximal end 18 to an apex 20 at a distal end 22. The cutting shell 12 is rotatable about a rotational axis A-A that extends through the apex 20. The cutting shell comprises a shell sidewall 24 having an exterior shell surface 26 spaced from a shell interior surface 28 that defines a shell thickness 30 therebetween. A plurality of spaced apart slits 32 oriented longitudinally along the shell 12 extend through the sidewall thickness 30.

The reamer 10 is preferably sized to allow access to tissue in and around the acetabulum. Alternatively, the reamer 10 can be sized and dimensioned to allow access to other tissue areas. In a preferred embodiment, the wall thickness 30 ranges from about 0.5 mm to about 2 mm. In a preferred embodiment, the shell 12 has an annular perimeter at the lower edge 16 having a diameter from about 20 mm to about 80 mm. The shell 12 also has a shell height 34 (FIG. 3A) that extends from the lower edge 16 to the apex 20. It is preferred that the height 34 ranges from about 10 mm to about 50 mm.

In an embodiment, a plurality of spaced apart cutting teeth 36 are positioned about the shell 12, each tooth extending outwardly from the exterior shell surface 26. In a preferred embodiment, a primary tissue cutting surface 38 is provided by each tooth 36 along a portion of an opening 40 that extends through the thickness 30 of the shell 12. In an embodiment, as illustrated in FIG. 1, each of the primary tissue cutting surfaces 38 is a portion of the shell wall 24 that extends at least partially over the opening 40. In a preferred embodiment, the primary tissue cutting surfaces 38 are oriented so that they outwardly extend from the exterior wall surface 26 of the shell 12. In an embodiment, the reamer teeth 36 may be constructed with a bent orientation, extending away from the exterior surface 26 of the shell 12 so that they do not lie in the same hemispherical curvature plane of the shell 12. In a preferred embodiment, each of the plurality of primary tissue cutting surfaces 38 is oriented in the same direction about the shell 12, either in a clockwise or counter clockwise cutting direction. Bending the reamer teeth 36 outwards, as shown in the preferred embodiment of FIG. 1, enables the reamer teeth 36 to "bite" into the tissue, creating a reamed cavity. Specific examples of various teeth and cutting surfaces that may be incorporated with the reamer of the present invention are disclosed in U.S. Pat. Nos. 7,850, 691, 8,784,422, and 9,351,740, all to Lechot et al., and U.S. Pat. No. 8,435,243 to White et al., all of which are assigned to the assignee of the present invention and incorporated herein by reference.

Figure 2:
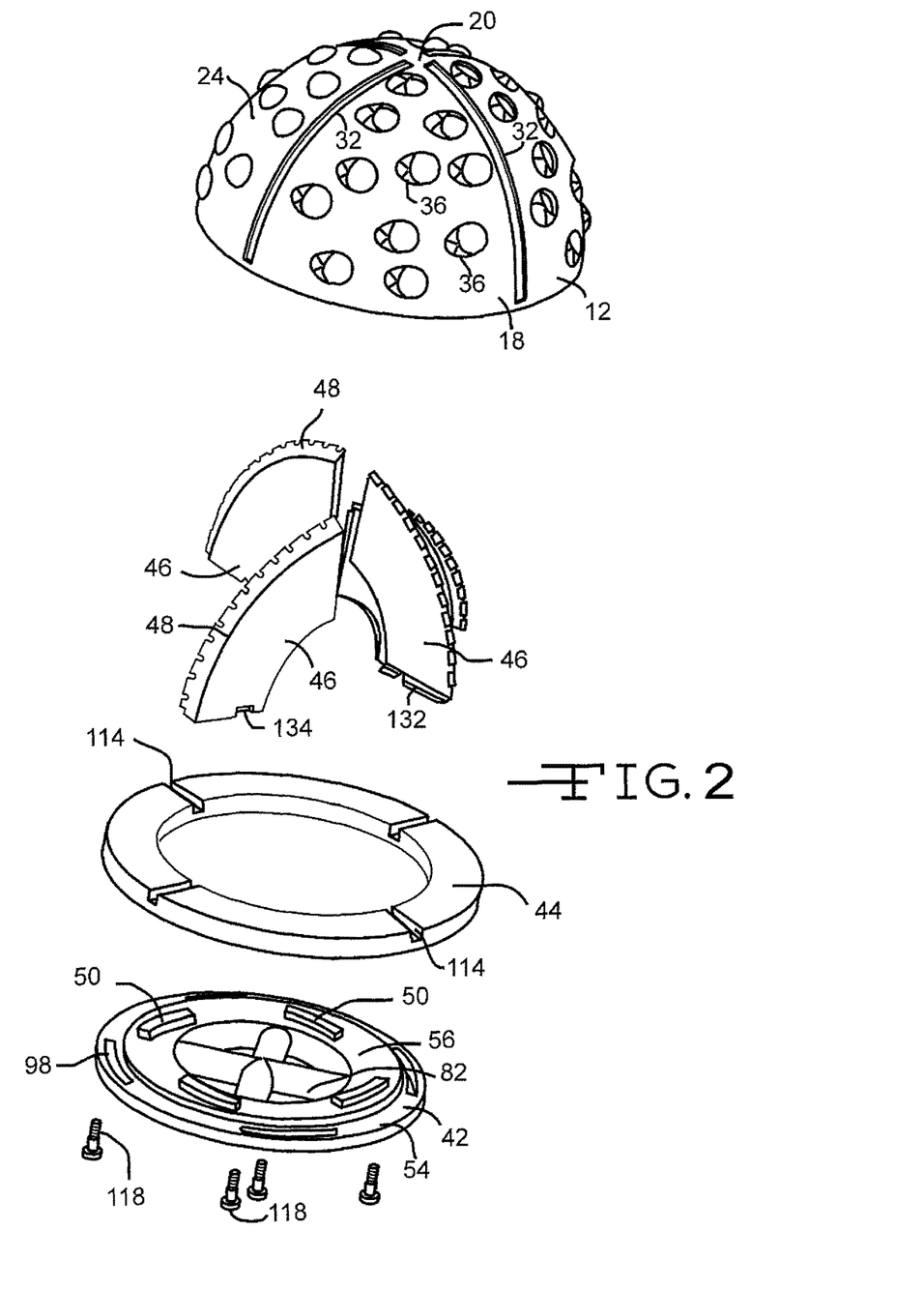
FIG. 2 is an exploded view of the embodiment of the reamer shown in FIG. 1.
Figure 6:
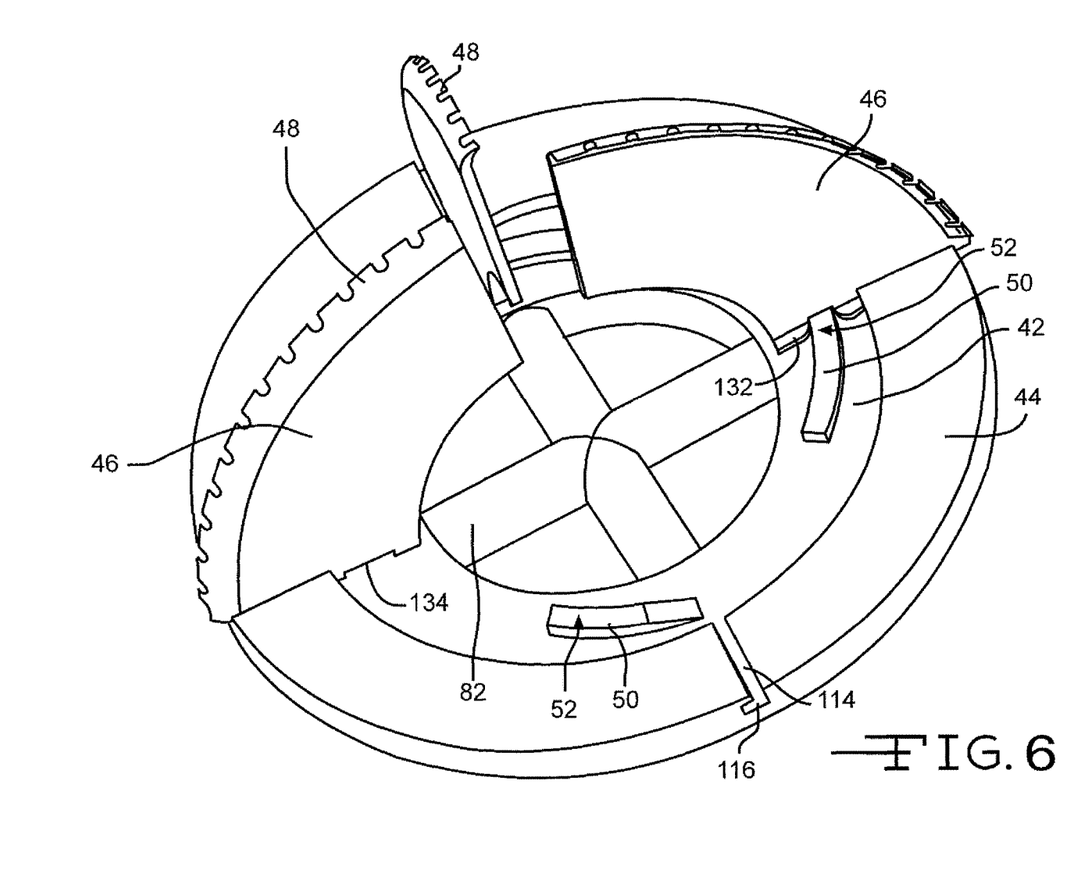
FIG. 6 shows an embodiment of a cam and ring subassembly with three second blades.

A cam 42 and ring 44 subassembly (FIG. 2) is positioned at the shell equatorial base 14. The subassembly provides a platform on which a plurality of spaced apart second blades 46, each having a secondary tissue cutting surface 48, is positioned. In addition, the subassembly enables movement of the second blades 46 from within the shell interior. As illustrated in FIGS. 2 and 6, the ring 44 positions each of the blades 46 in an upright position within the interior of the shell 12. The cam 42, which comprises a plurality of spaced apart ridges 50, each having a ramped surface 52, is positioned so that each ridge 50 is in contact with one of the plurality of second blades 46. As the cam 42 is rotated in either a clockwise or counterclockwise direction, the ramped ridges 50 cause the second blades 46 to raise outwardly, away from the rotational axis as they extend through a respective shell slit 32. Rotation of the cam 42 in an opposite direction causes the second blades 46 to retract into the shell interior, back to the starting position illustrated in FIG. 3A.

In an embodiment, when the second blades 46 are in the extended position, as illustrated in FIG. 3B, the secondary tissue cutting surfaces 48 may extend further away from the shell exterior surface 26 than the primary tissue cutting surfaces 38 of the teeth 36. This preferred orientation helps ensure that the secondary tissue cutting surfaces 48 of the second blades 46 are in contact with tissue or bone that is to be cut. Alternatively, when the second blades 46 are in the extended position, the secondary and primary tissue cutting surfaces 48, 38, respectively, may extend at about the same distance from the shell exterior surface 26.

Figure 4:
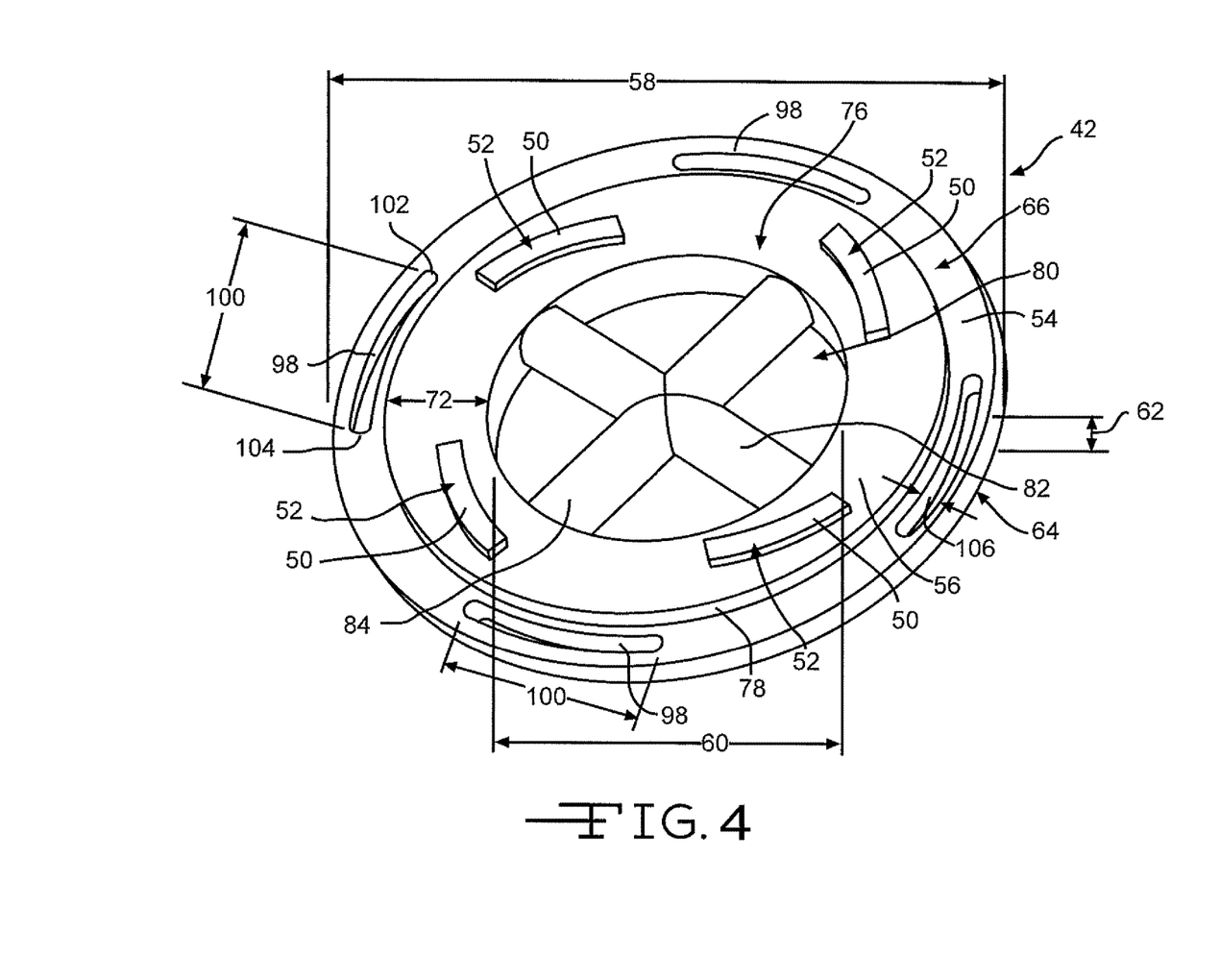
FIG. 4 illustrates an embodiment of the cam with a cross-bar driver interface.
Figure 4A:
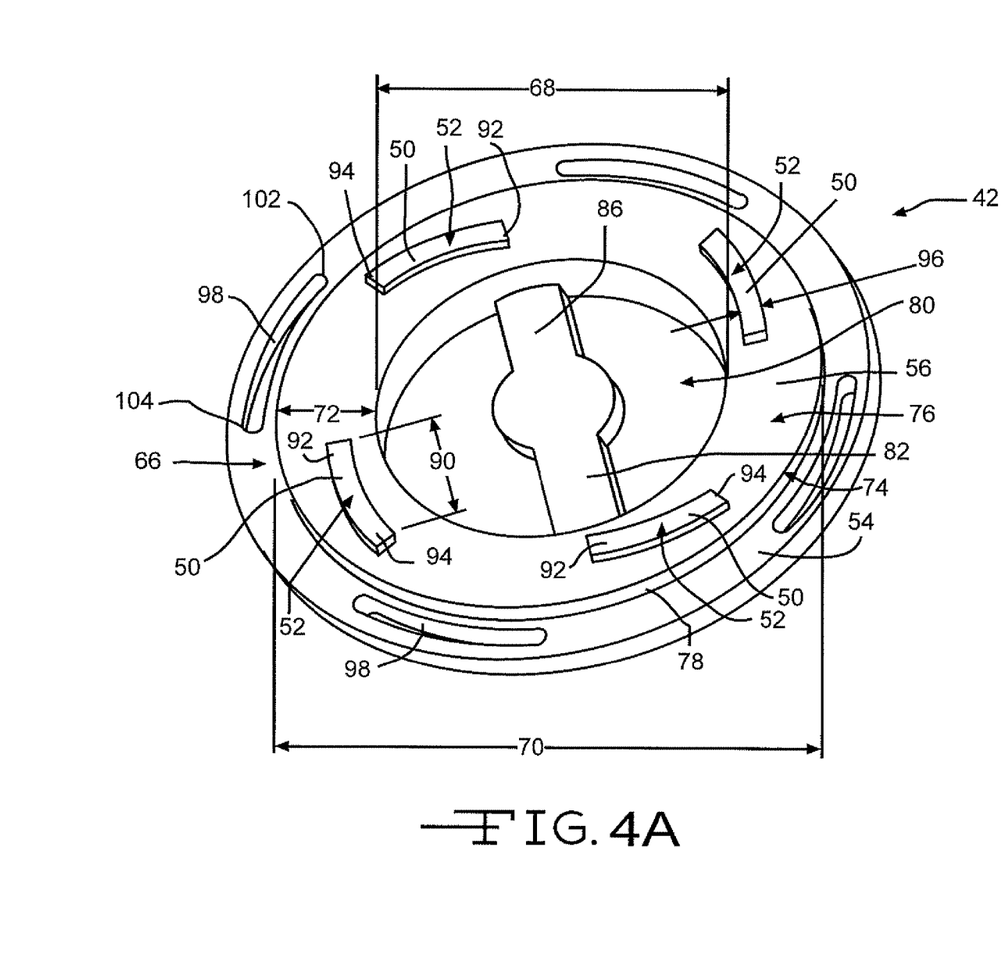
FIG. 4A illustrates an alternate embodiment of the cam with a bar and boss driver interface.

FIGS. 4 and 4A illustrate embodiments of the cam 42. In a preferred embodiment, the cam 42 is of a unitary body construction having an annular shape. As illustrated, the cam 42 comprises a base platform 54 that meets and joins an upper platform 56. In a preferred embodiment, the base platform 54 has an annular shape comprising a base platform outer diameter 58 that ranges from about 20 mm to about 80 mm and a base platform inner diameter 60 that ranges from about 10 mm to about 70 mm. In an embodiment, the base platform outer diameter 58 defines the outer diameter of the cam 42. In addition, the base platform 54 has a thickness 62 that extends from a base platform proximal surface 64 to a base platform distal surface 66.

As shown in FIGS. 4 and 4A, the upper platform 56 extends in a distal direction from the base platform distal surface 66. In a preferred embodiment, the upper platform 56 comprises an annular shape having an upper platform inner diameter 68 that extends to an upper platform outer diameter 70. An upper platform width 72 spans between the outer and inner upper platform diameters 70, 68. In addition, the upper platform 56 has an upper platform height 74 that extends upwardly from the base platform distal surface 66 to an upper platform distal surface 76 along rotational axis A-A. As shown in FIGS. 4 and 4A, a step 78 is formed between the base platform 54 and the upper platform 56. The step having height 74. In a preferred embodiment, the inner diameters 60, 68 of the base and upper platforms 54, 56 are co-axially aligned about rotational axis A-A. In addition, the inner diameters 60, 68 of the base and upper platforms 54, 56 are dimensioned to be about the same size. Thus, a throughbore 80 extends along rotational axis A-A through the cam 42. A reamer driver interface 82 comprising at least one strut 84 (FIG. 4), but preferably two struts 84 in a cross bar configuration, a bar and boss 86 configuration (FIG. 4A), or a ring-and-strut combination (not shown), is positioned within the throughbore 80 spanning to opposed or spaced apart surfaces of the base and upper platform surfaces 54, 56 at their inner diameters 60, 68.

As illustrated in FIGS. 4, 4A, 5 and 6, the plurality of spaced apart cam ridges 50 extend distally from the upper platform distal surface 76. In a preferred embodiment, each ridge 50 is positioned within the boundary of the upper platform width 72, spaced from the inner and outer diameters of the upper platform 56. Each ridge 50 comprises a maximum height 88 (FIG. 5) that extends along the rotational axis A-A from the upper platform distal surface 76 to the ridge surface 52. In addition, each of the ridges 50 comprises a length 90 that extends along the upper platform surface 76 from a ridge first end 92 to a ridge second end 94 (FIG. 4A). A ridge width 96 (FIG. 4A) extends perpendicular to the length 90. In a preferred embodiment, the ridges are constructed so that the height of the ramped surface gradually increases in an upward or distal direction from the ridge first end 92 to the ridge second end 94.

As shown in FIGS. 4 and 4A, the plurality of ridges 50 is positioned in an annular orientation about the upper platform distal surface 76. As illustrated, the plurality of ridges 50 is preferably positioned in a clockwise orientation about rotational axis A-A. Each of the ridges 50 is positioned so that the second end 94 of a ridge 50 is positioned adjacent the first end 92 of the next ridge 50. In addition, each ridge 50 is preferably curved. As shown in FIGS. 4 and 4A, each ridge 50 has a curvature as it extends from the first to the second ridge ends 92, 94. In a preferred embodiment, each ridge 50 has a concave curvature with respect to the rotational axis A-A. This preferred ridge orientation helps ensure that each of the second blades 46 is raised or lowered in a simultaneous manner to about the same height with respect to the exterior shell surface.

As illustrated in FIGS. 4 and 4A, four spaced apart ridges 50 are shown extending from the upper platform surface 76 annularly positioned about the rotational axis A-A. While four ridges 50 are preferred, it is contemplated that the cam 42 could be constructed having a greater or lesser number of ridges 50. Furthermore, it is preferred that the ridges 50 are positioned diametrically opposed from each other. This preferred orientation helps extend and lower the second blades 46 simultaneously through their respective shell slit 32.

Figure 8:
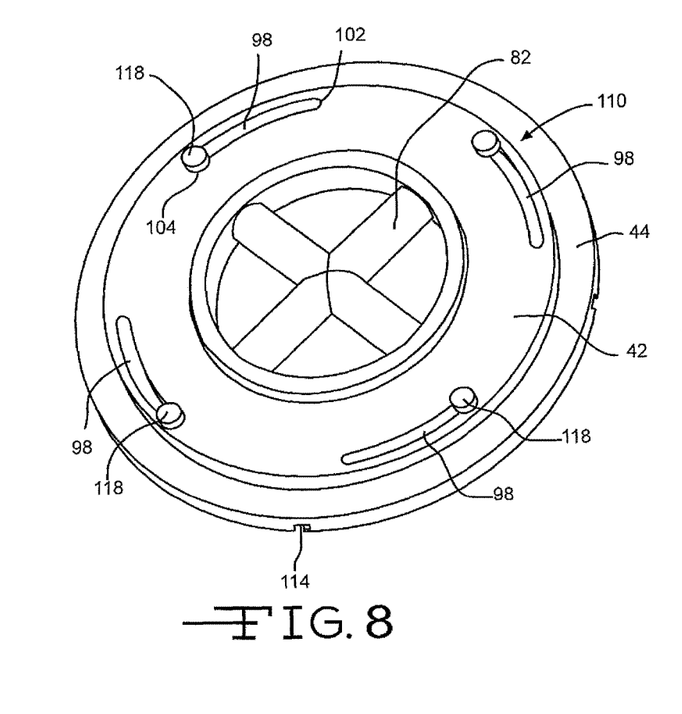
FIG. 8 shows a perspective view of the proximal side of the cam and ring subassembly.

As illustrated in FIGS. 4, 4A, and 8, a plurality of spaced apart slots 98 extend through the thickness 62 of the base platform 54 of the cam 42. In a preferred embodiment, each slot 98 is positioned within the boundary of the base platform width, spaced from the outer diameters 70, 58 of the upper and base platforms 56, 54, respectively. Each slot 98 comprises a length 100 (FIG. 4) that extends from a slot first end 102 to a slot second end 104. A slot width 106 extends perpendicular to the length 100. As shown in FIGS. 4, 4A, and 8, each slot 98 is positioned in a clockwise orientation about the base platform 54, oriented lengthwise from the first slot end 102 to the second slot end 104. In an embodiment, each slot 98 is positioned annularly about the base platform 54 in a diametrical opposed orientation to another one of the slots 98. In addition, each slot 98 is positioned between two spaced apart ridges 50 as the slots 98 and ridges 50 lie within the respective upper and base platforms 56, 54. In a preferred embodiment, each slot 98 is positioned so that its first slot end 102 is radially aligned with the second end 94 of a first ridge 50. In addition, the second end 104 of the slot 98 is preferably radially aligned with the first end 92 of an adjacent ridge 50. In an embodiment, the number of ridges 50 and slots 98 may be the same. In an embodiment, the number of ridges 50 and second blades 36 may be the same. Thus, for example, if the cam 42 is constructed with six ridges 50, the cam 42 could comprise six slots 98 and six, second blades 36. This preferred orientation of a slot 98 with respect to an adjacent ridge 50 helps ensure that each of the second blades 46 travels the same distance as it is raised and lowered with respect to the shell exterior surface 26. The length 100 of the slot 98 determines the length of rotational travel of the ramped ridge 50 which thus determines the distance a second blade 46 is raised and lowered through a respective shell slit 32.

The ring 44 (FIGS. 1, 2, 5, 6 and 8) is preferably positioned about the cam base platform 54. In a preferred embodiment the ring 44 is of an annular shape that is positioned circumferentially around the cam upper platform 56. As shown, the ring 44 comprises a ring thickness 108 that extends between a ring proximal surface 110 and a ring distal surface 112. The ring is positioned about the cam upper platform 56 so that the ring proximal surface 110 is in contact with the base platform distal surface 66.

Figure 5:
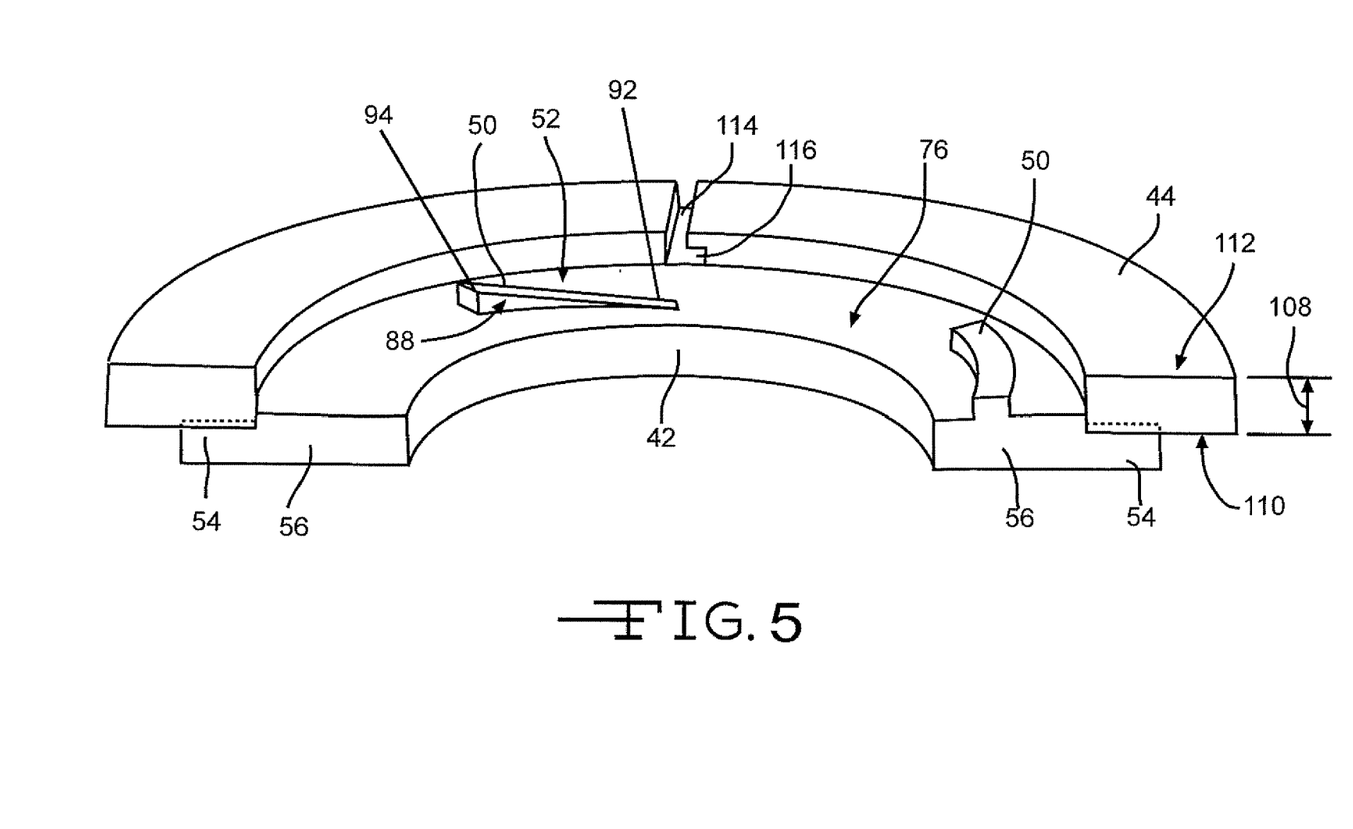
FIG. 5 illustrates a cross-sectional view of an embodiment of the cam and ring subassembly without the driver interface.

A plurality of spaced apart ring slots 114 extend both through the ring distal surface 112 and at least partially through the ring thickness 108. As shown in FIGS. 2, 5, and 6, each ring slot 114 extends lengthwise across the width of the ring 44. In a preferred embodiment, the length of each ring slot 114 is positioned about parallel to the width of the ring 44. In an embodiment, the ring slots 114 may comprise a traverse portion 116 that extends about perpendicular from the slot 114 within the thickness 108 of the ring 44. Thus, the ring slot 114 may be constructed having a cross-section oriented perpendicular to the ring thickness 108 having an "L" shape.

In an embodiment, the cam and ring subassembly is positioned at the shell base 14. As illustrated in FIG. 1, the ring 44 is preferably positioned at least partially within the shell interior at the base 14 and is anchored thereto. In a preferred embodiment, the proximal surface 110 of the ring 44 is positioned about parallel with the equatorial base of the shell 12. More preferably, the ring proximal surface 110 may be positioned about flush with the lower edge 16 of the shell 12. In addition, a plurality of fasteners 118 (FIGS. 1, 2 and 8) connect the cam 42 to the ring 44. As illustrated in FIGS. 1 and 8, each fastener 118 is positioned through the base platform slot 98 and within the thickness 108 of the ring 44, thereby slidably securing the cam 42 to the ring 44 such that the cam 42 rotates with respect to the ring 44 as the fasteners 118 travel within a slot 98. In an embodiment, the clockwise or counterclockwise rotation of the cam 42 with respect to the ring 44 is limited by the length of the base platform slot 98 within which the fastener 118 moves back and forth.

Figure 7:
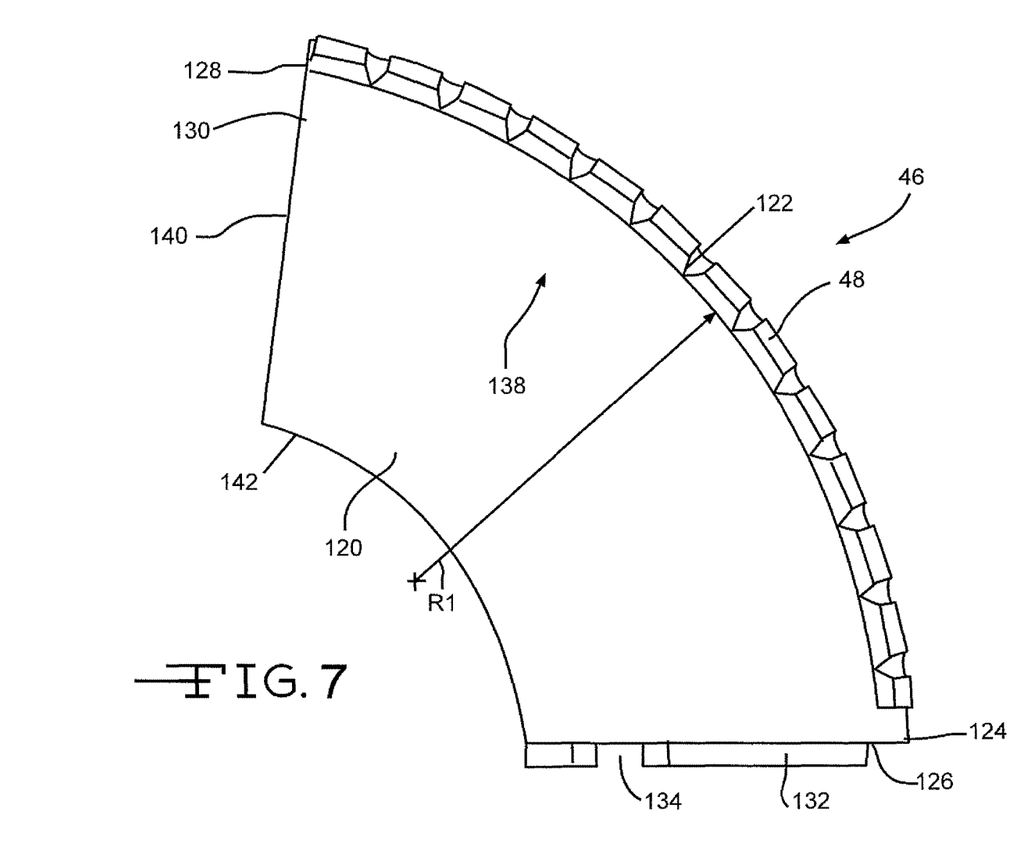
FIGS. 7 and 7A illustrate different views of an embodiment of a second blade.
Figure 7A:
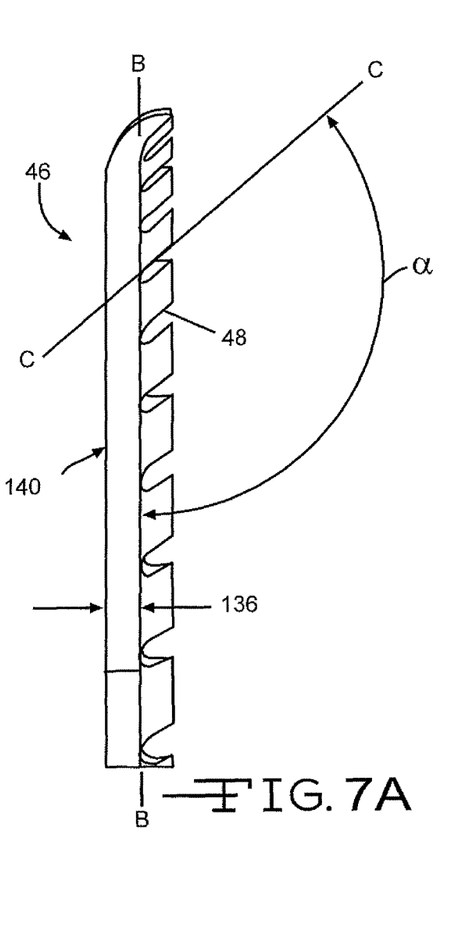

FIGS. 7 and 7A illustrate an embodiment of a second blade 46. As shown, each second blade 46 comprises a sidewall 120 having a first end 122 with a curved shape. The second blade sidewall 120 has a sidewall thickness 136 that extends between opposing first and second sidewall surfaces 138, 140. More preferably, the second blade first end 122 has a convex shape with a radius of curvature $R_1$. In an embodiment, radius of curvature $R_1$ is greater than the radius of curvature formed by the hemispherical shell 12 with respect to the rotational axis A-A. In a preferred embodiment, $R_1$ may range from about 1 cm to about 10 cm. In an embodiment, as illustrated in FIG. 7, the first sidewall end 122 is constructed having a partially hemispherical shape that extends from a blade base 124 at a second blade proximal end 126 to a blade apex 128 at a second blade distal end 130. In an embodiment, the blade base 124 is dimensioned to be received within the ring slot 114. Furthermore, a tang 132 extends outwardly from the blade base 124. The tang 132 comprises a portion of the blade sidewall that extends along the blade base 124. In an embodiment, the tang 132 may be oriented about perpendicular to the blade sidewall 120, as shown in FIG. 6. In addition, a notch 134 extends at least partially through the thickness of the tang 132 at the blade base 124. The tang 132 is designed to be received within the traverse portion 116 of the ring slot 114 to help position the second blade 46 in an upright orientation, i.e., such that the second blade apex 128 extends towards the shell apex 20, within the shell interior.

In an embodiment, as illustrated, in FIGS. 7 and 7A, the blade 46 may be constructed having an annular sector shape. In this embodiment, the second blade sidewall 120 comprises a fourth end 142 having a second radius of curvature $R_2$. In an embodiment, radius of curvature $R_2$ is less than the radius of curvature $R_1$. In a preferred embodiment, radius of curvature $R_2$ may range from about 0.5 cm to about 4 cm. Nevertheless, the second blade 46 may be constructed of a variety of non-limiting shapes provided that the blade 46 comprises a base edge 126 dimensioned to be received within the ring slot 114 and a curved first end 122 that comprises the secondary cutting tissue surface 48.

As illustrated in FIGS. 6, 7, and 7A, the first end 122 of the second blade 46 comprises the secondary tissue cutting surface 48. The secondary cutting surface 48 may be constructed as a serrated cutting surface or, alternatively, as a continuous non-serrated cutting surface. As shown in FIGS. 7 and 7A, the secondary cutting surface 48 is preferably bent at an angle with respect to the plane of the blade sidewall 120. In a preferred embodiment, the secondary cutting surface 48 is bent at an angle α that ranges between 20° to about 60°, more preferably about 45°. As illustrated in FIG. 7A, the secondary cutting surface angle is measured between a first imaginary plane B-B that is co-planar to the blade sidewall 120 and a second imaginary plane C-C that is co-planar to the secondary tissue cutting surface 48.

In an embodiment, the secondary cutting surfaces 48 of the second blades 46 and the primary cutting surfaces 38 of the teeth 36 are oriented about the exterior surface 26 of the shell 12 in opposition to each other. In other words, each of the respective primary and secondary cutting surfaces 38, 48 are positioned above the shell exterior surface 26 such that they face away from each other. For example, if the primary cutting surfaces 38 are oriented about the shell 12 in a clockwise direction, the secondary cutting surfaces 48 of the retractable blades 46 are oriented in a counterclockwise direction with respect to the shell exterior surface 26. This preferred orientation of the secondary cutting surfaces 48 with respect to the primary cutting surfaces 38 enables the reamer 10 of the present invention to cut bone or tissue in both clockwise and counterclockwise directions. That is without removing or repositioning the reamer 10 during a surgical procedure. Furthermore, since the secondary cutting surface 48 of the second blade 46 may be constructed having different cutting surfaces, the reamer 10 of the present invention could be used to cut or scrape tissue and bone without removing the reamer during a surgical procedure. For example, the first tissue cutting surfaces 38 of the teeth 36 could be used first to cut bone and tissue in a clockwise direction, after which the secondary cutting surfaces 48 could be extended to scrape the tissue and bone in a counterclockwise direction, thereby creating a smoother cut surface.

FIG. 6 illustrates an embodiment in which three, second blades 46 are positioned within the cam 42 and ring 44 subassembly. As shown, each of the second blades 46 is positioned in an upright orientation about the annular ring 44. More preferably, as shown, each of the second blades 46 is positioned in an upright orientation so that their apex 126 extends towards the shell apex 20. The blade base 124 and tang 132 are received within the corresponding ring slot 114 and traverse portion 116. Thus, by positioning each second blade 46 within the ring slot 114, the plurality of blades 46 is oriented in an upright position with the second blade sidewall thickness 136 oriented about perpendicular to the rotational axis A-A. In addition, the second blades 46 are positioned within the ring 44 so that the curved convex blade first end 120 faces away from the rotational axis A-A.

In addition, as illustrated in FIG. 6, at least a portion of each of the second blades 46 is positioned in contact with the upper platform distal surface 76. As shown, the blade base 124 is preferably positioned parallel with the upper platform distal surface 76. Furthermore, each second blade 46 is preferably positioned with respect to the cam 42 such that the ridge 50 is received within the notch 134 that extends perpendicularly through the thickness of the tang 132. Thus, rotation of the cam 42 in either a clockwise or counter clockwise direction with respect to the shell equatorial base 14, causes the ramped surfaces 52 of the ridges 50 to come into contact with the blade base 124, thus raising the secondary tissue cutting surface 48 through the shell slit 32. Then, rotation in the other of the clockwise or counter clockwise direction causes the secondary blades to lower or retract below the shell exterior surface 26.

Thus, it has been shown that the reamer 10 of the present invention provides for more efficient tissue and bone cutting. The features of the present invention, such as the extendable and retractable secondary cutting blades 46 provide an additional tissue cutting structure that selectively removes tissue and bone and thus, provides a smoother reamed surface than is possible with prior art reamers. Furthermore, the possibility of improper positioning or excessive wear of an implant is minimized.

It is appreciated that various modifications to the inventive concepts described herein may be apparent to those of ordinary skill in the art without departing from the spirit and scope of the present invention as defined by the appended claims.

What is claimed is:

1. A reamer, which comprises:
   a) a cutting shell having a shell wall with spaced apart exterior and interior shell surfaces, a shell wall thickness therebetween, the shell having a curvature comprising at least a portion of a first hemisphere from an apex to a lower edge, the cutting shell being rotatable about a rotational axis that extends through the apex, wherein at least one slit extends through the shell wall thickness;
   b) a plurality of cutting teeth, each having a primary tissue cutting surface, wherein the primary tissue cutting surface extends outwardly from the exterior surface of the shell;
   c) a ring secured to the shell lower edge, the ring having a ring thickness that extends from a ring proximal surface to a ring distal surface, a ring slot having a slot length and a slot depth, wherein the slot depth extends through the ring distal surface and at least partially through the ring thickness;
   d) a second blade comprising a second blade sidewall having a sidewall first end spaced from a sidewall second end, wherein the sidewall first end comprises a secondary tissue cutting surface, and wherein the sidewall second end is received within the ring slot;
   e) a cam having opposed proximal and distal cam surfaces, wherein the cam is rotatably secured to the ring proximal surface adjacent to the shell lower edge, a ridge having a ramped surface extending from the cam distal surface, wherein the second blade sidewall second end is in contact with the ridge ramped surface; and
   f) wherein rotation of the cam in either a clockwise or counterclockwise first direction causes the second blade sidewall second end to ride up the ridge ramped surface thereby causing the secondary tissue cutting surface to extend through the at least one slit, and wherein rotation of the cam in an opposite second direction causes the second blade sidewall second end to ride down the ridge ramped surface thereby causing the secondary tissue cutting surface to retract within the shell interior.

2. The reamer of claim 1 wherein the second blade sidewall first end is constructed having a curved shape.

3. The reamer of claim 2 wherein the second blade sidewall first end comprises a convex shape with respect to the rotational axis A-A.

4. The reamer of claim 1 wherein the second blade is of an annular sector shape.

5. The reamer of claim 1 wherein the secondary tissue cutting surface comprises a serrated or non-serrated cutting surface.

6. The reamer of claim 1 wherein the at least one slit has a slit length that extends through the shell thickness from a first slit end to a second slit end, wherein the first slit end is spaced from the shell apex and the second slit end is spaced from the shell lower edge.

7. The reamer of claim 1 wherein the cam comprises an upper cam platform having an annular shape with an upper cam platform outer diameter that extends from a base cam platform having an annular shape with a base cam platform outer diameter, wherein the base cam platform outer diameter is greater than the upper cam platform outer diameter.

8. The reamer of claim 7 wherein a base cam platform slot having a base cam platform slot depth and a base cam platform slot length resides within the base cam platform, wherein the slot depth extends through a base cam platform thickness that extends along rotational axis A-A and the base platform length extends in an annular orientation about the rotational axis A-A within the base cam platform thickness.

9. The reamer of claim 7 wherein the ridge extends from a distal surface of the upper cam platform.

10. The reamer of claim 1 wherein the cam comprises a throughbore that extends through the cam proximal and distal surfaces along the rotational axis A-A.

11. The reamer of claim 10 wherein a driver interface selected from the group consisting of a cross bar configuration, a bar and boss configuration, and a ring-and-strut combination, is positioned within the cam throughbore.

12. The reamer of claim 1 wherein the ring slot length extends perpendicular to the rotational axis A-A.

13. The reamer of claim 1 wherein the sidewall first end is curved having a sidewall first end radius of curvature that originates from the rotational axis A-A.

14. The reamer of claim 13 wherein the sidewall first end of the second blade has a radius of curvature that is greater than a shell radius of curvature formed by the exterior shell surface with respect to the rotational axis A-A.

15. The reamer of claim 13 wherein the sidewall first end radius of curvature ranges from about 1 cm to about 10 cm.

16. The reamer of claim 1 wherein the secondary tissue cutting surface is positioned at a secondary cutting angle with respect to the second blade sidewall, the secondary cutting angle defined as the angle that extends between an imaginary plane B-B that is co-planar to the second blade sidewall and an imaginary plane C-C that is co-planar to the secondary tissue cutting surface.

17. The reamer of claim 16 wherein the secondary tissue cutting angle ranges from about 20° to about 60°.

18. The reamer of claim 1 wherein the primary and secondary tissue cutting surfaces are oriented in opposition to each other.

19. The reamer of claim 1 further comprising a plurality of spaced apart ridges that extend outwardly from the cam distal surface, wherein the plurality of ridges are arranged in an annular orientation about the rotational axis A-A.

20. The reamer of claim 1 wherein the second blade comprises a tang that extends outwardly from the blade sidewall second end, wherein the tang is received within the ring slot.

21. The reamer of claim 20 wherein the tang is oriented at an angle from the second blade sidewall.

22. The reamer of claim 20 wherein a notch dimensioned to receive the ridge extends perpendicularly through a thickness of the tang.

\* \* \* \* \*